US005574186A

United States Patent [19]
Boudreau et al.

[11] Patent Number: 5,574,186
[45] Date of Patent: Nov. 12, 1996

[54] ENANTIOSELECTIVE SYNTHESIS OF CYCLIC AMINO ALCOHOLS

[75] Inventors: Charles Boudreau, Salem, N.H.; Richard D. Tillyer, Scotch Plains; David M. Tschaen, Holmdel, both of N.J.

[73] Assignee: Merck & Co., Inc., Rahway, N.J.

[21] Appl. No.: 401,050

[22] Filed: Mar. 8, 1995

[51] Int. Cl.$^6$ .................................................. C07C 209/40
[52] U.S. Cl. .......................... 564/393; 564/415; 564/428
[58] Field of Search .................................. 564/393, 415

[56] References Cited

PUBLICATIONS

Blaser, H.-U., *Chem. Rev.* (1992), 92, 935–952.
Kano, S., et al., *Chem. Lett.* (1987) 1531–1534.
Gmeiner, P., et al., *Tetrahedron Lett.* (1993) 34, 4325–4326.
Oppolzer, W. et al., *J. Am. Chem. Soc.* (1992), 14, 5900–5902.
Lohray, B. B., et al., *Tetrahedron Lett.* (1989), 30, 2623–2626.
Cho, B. T., et al., *Tetrahedron Asymeetry* (1992), 3, 341–342.
Fisher, G. B., et al., *Tetrhedron lett.*(1993), 34, 7693–7696.
Beardsley D. A., *Tehrahedron Lett.* (1994) 35, 1511–1514.

*Primary Examiner*—Brian M. Burn
*Attorney, Agent, or Firm*—Sylvia A. Ayler; Mark R. Daniel

[57] ABSTRACT

There is disclosed a novel process for the enantioselective synthesis of chiral amino alcohols from keto oxime ethers, which are derived from cyclic ketones, via catalytic asymmetric reduction, employing oxazaborolidine-borane complex (OAB-BH$_3$). In this catalytic reduction process two chiral centers are created in a single step with high levels of stereoselectivity.

7 Claims, No Drawings

ENANTIOSELECTIVE SYNTHESIS OF CYCLIC AMINO ALCOHOLS

BACKGROUND OF THE INVENTION

The development of new methods for the enantioselective synthesis of chiral amino alcohols is of continuing importance, since these compounds have interesting biological activity and have enormous potential as chiral ligands in metal-mediated organic reactions. See Blaser, H.-U., *Chem. Rev.* (1992), 92, 935. It is known that many amino alcohols can be derived from the available amino acids. See Kano, et al., *Chem Lett.* (1987), 1531 and Kano, et al., *Tetrahedron Lett.* (1993), 34, 4325. Additionally, several highly stereoselective synthesis of chiral amino alcohols/acids have been reported using chiral auxiliaries. However, these procedures generally involve multi-step reactions. See Mulzer, J; Altenbach, H.-J.; recent example see Oppolzer, W.; Tamura, O.; Sundarababu, G.; Signer, M.; *J. Am. Chem. Soc.* (1992), 114, 5900. Preparation of the novel compounds of this class requires asymmetric synthesis, preferably using a chiral starting materials. Although advances have been made in this area, (See Lohray et al., Tetrahedron Lett. (1989), 30 2623; Cho et al., Tetrahedron Asymmetry (1992), 3, 341; Fisher et al., Tetrahedron Lett. (1993), 34, 7693; Beardsly Tetrahedron Lett. (1994), 35 1511), new synthetic methods must be developed to access chiral amino alcohols that are not available using current technology.

An attractive approach to the synthesis of chiral amino alcohols involves reduction of keto-oximes. This approach has been used previously in the literature for the preparation of racemic amino alcohols but has not been successfully applied to the enantioselective preparation of cyclic amino alcohols.

SUMMARY OF THE INVENTION

This invention is concerned with a novel process for the stereoselective synthesis of cyclic amino alcohols, in particular, cyclic cis amino alcohols, wherein both enantiomers (R,S, and S,R,) are available, from keto oxime ethers via catalytic asymmetric reduction using an oxazaborolidine-borane complex (OAB-BH$_3$). In this catalytic reduction process two chiral centers are created in a single step with high levels of stereoselectivity. Thus, it is an object of the present invention to provide a process for the stereoselective synthesis of cyclic amino alcohols.

DETAILED DESCRIPTION OF THE INVENTION

One embodiment of this invention for the preparation of a compound represented by formula Ia or Ib:

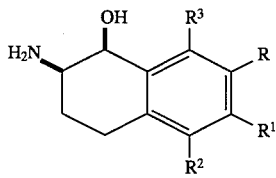

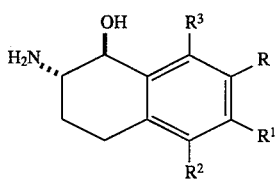

the individual diastereomers, the individual enantiomers or mixtures thereof, or acceptable salt whereof, wherein:

R, R$^1$, R$^2$ and R$^3$ are independently H, C1 to C10 alkyl, O-alkyl, alkylamino, thioalkyl, alkene, cycloalkyl or halogen;

comprises the steps of adding, over a course of about 3 to about 6 hours, a solution, containing a solvent and from about 0.05M to about 5.0M of a keto-oxime ether of the formula II:

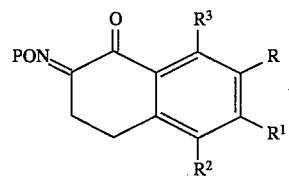

wherein P is H, t-butyldimethylsilyl (TBS) t-butyldiphenylsilyl (TBDPS), acetate, benzoate, benzyl, paramethoxybenzyl (PMB), or alkyl; and R, R$^1$, R$^2$ and R$^3$ are independently H, C1 to C10 alkyl, O-alkyl, alkylamino, thioalkyl, alkene, cycloalkyl or halogen;

to a stirred and chilled solution of about 2 to about 30mol % of an OAB-BH$_3$ complex and excess BH$_3$.SMe$_2$ in a solvent, stirring the mixture, heating the mixture until a substantial amount of formula Ia to Ib is produced and isolating the compound so produced.

A second embodiment of this invention for the preparation of a compound represented by formula Ia, or Ib:

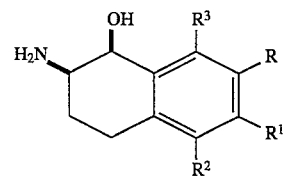

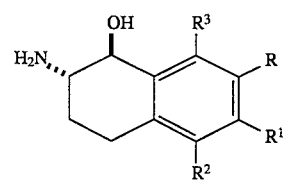

the individual diastereomers, the individual enantiomers or mixtures thereof, or acceptable salt thereof, wherein:

R, R$^1$, R$^2$ and R$^3$ are independently H, C1 to C10 alkyl, O-alkyl, alkylamino, thioalkyl, alkene, cycloalkyl or halogen; comprises the steps of simultaneously adding an excess, from about 2 to about 4 equivalents, of BH$_3$.SMe$_2$ and from about 0.05M to about 0.5M of a keto-oxime ether of structural formula II:

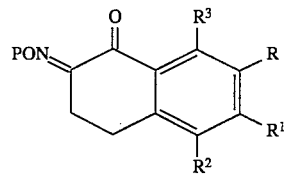

wherein:

P is H, TBS, TBDPS, acetate, benzoate, benzyl, paramethoxybenzyl (PMB), or alkyl; and R, R$^1$, R$^2$ and R$^3$ are independently H, C1 to C10 alkyl, O-alkyl, alkylamino, thioalkyl, alkene, cycloalkyl or halogen;

over the course of 2 to 6 hours, to from about 2 to about 30 mol % of a stirred and chilled solution of OAB-BH$_3$ catalyst, stirring the mixture, heating the mixture until a substantial amount of formula I is produced and isolating the compound so produced.

The novel process of this invention can be depicted as shown in scheme I below:

SCHEME I

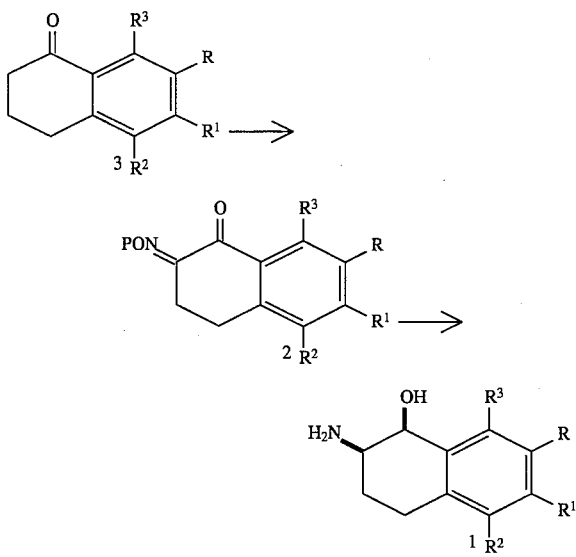

Cyclic (S,R)-cis amino alcohols 1 (or the enantiomeric (R,S)-cis amino alcohols), the individual diastereomers, the individual enantiomers or mixtures thereof, or acceptable salt thereof, wherein:

R, R$^1$, R$^2$ and R$^3$ are independently H, C1 to C10 alkyl, O-alkyl, alkylamino, thioalkyl, alkene, cycloalkyl or halogen; and P is H, TBS, TBDPS, acetate, benzoate, benzyl, paramethoxybenzyl (PMB), or alkyl.

are stereoselectively synthesized from keto oxime ethers 2, which are derived from cyclic ketones 3, via catalytic asymmetric reduction, utilizing oxazaborolidine-borane complex (OAB-BH$_3$) 4 (or its enantiomer)

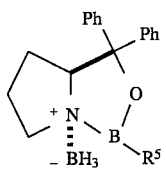

wherein: R$^5$ is C1 to C5 alkyl or aryl.

The cyclic keto-oxime ethers can be prepared by conventional methods known in the art. For example, the keto-oxime ethers in the instant invention were prepared in high yield from the corresponding cyclic ketones 3 via α-oximation (isoamyl nitrite-HCL or NaOEt (See Touster, O., *Organic Reactions*, Vol. VII, Wiley, (1966), P. 327) followed by O-protection, wherein the O-protecting group is H, TBS, TBDPS, acetate, benzoate, benzyl, paramethoxybenzyl (PMB), or alkyl and the like, preferably TBS or TBDPS. O-protection is carried out by conventional methods known in the art.

The reduction can be carded out using O-protected keto-oxime ethers, for example keto-oxime TBS ethers derived from substituted 1-tetralones as in 2 of Scheme I, wherein R, R$^1$, R$^2$ and R$^3$ are as described above, via traditional methods known in the art. Complete reduction of the keto-oxime ether to the corresponding amino alcohols 1 requires i) keto group reduction, ii) C-N double bond reduction and iii) N-O reduction.

In general the oxazaborolidine-borane catalyzed reduction begins with the ketone reduction occurring within about 30 minutes to about 3 hours, at a temperature of about –30° C. to about 0° C., with partial C-N reduction. Complete C-N reduction is achieved at room temperature and heating is required-to achieve N-O reduction.

In one embodiment of the invention, the instant cyclic amino alcohols can be produced by slowly adding, over about 3 to about 6 hours, a solution of the keto-oxime ether, from about 0.05M to about 5.0M, to a stirred and chilled mixture, from about –30° C. to about 0° C., s preferably about –15° C. to about –25° C., of OAB-BH$_3$ complex, from about 2 to about 30 mol %, and excess BH$_3$.SMe$_2$, from about 1.0 to about 4 equivalent, in a solvent belonging to the group consisting of toluene, ethylene chloride, THF, hexane, and the like, preferably, toluene. The mixture is stirred at from about –30° C. to about 0° C. for about 0 to about 2 hours and at room temperature for about 0 to about 2 hours and then heated at a temperature of about 50° C. to about 90° C. for about 12 to 48 hours.

An alternative embodiment of the invention is to slowly add the BH$_3$.SMe$_2$, to a mixture of the ketone and OAB-BH$_3$ catalyst. The preferred embodiment of the invention is the simultaneous slow addition of BH$_3$.SMe$_2$ and ketone to the OAB-BH$_3$ catalyst.

The product, compound 1, can be recovered from the mixture by conventional means which are commonly used for the recovery of other known biologically active substances. For example, compound 1 is isolated from the heated mixture utilizing a solvent workup wherein a solvent such as methanol, ethanol, propanol, water, and the like is added to the mixture, the mixture refluxed and then concentrated. The residue is redissolved in the solvent, refluxed and concentrated to give a crude oil which is purified by silica gel chromatography to give the amino alcohols as a mixture of diastereomers. Chiral HPLC analyses were performed on amino alcohols before and after purification. Baseline separation of diastereomers and enantiomers was achieved in each case.

In the case where keto oxime ethers with aromatic substituents, wherein R1 is O-alkyl, are employed the OAB-BH3 catalysed reduction is performed at about –30° C. to about 0° C., followed by warming to room temperature and solvent workup. The crude mixture is then hydrogenated with 2 to 7% Pt/C, MeOH-NH$_4$OH to effect N-O reduction while avoiding benzylic de-oxygenation.

Analytical Methods

The analytical methods generally employed in the present invention, though non-limiting, were as follows:

High Performance Liquid Chromatography

HPLC was performed using a Thermo Separations Products P 4000 pumping system equipped with a UV 2000 detector. The system was fitted with a Crownpak CR(+) column (150 mm×4 mm) for analysis of enantiomer/diastereomer mixtures.

Silica Gel Chromatography.

Flash column chromatography was performed using Merck silica gel 60 (230–400 mesh). The fractions were analyzed by thin layer chromatography using Merck silica gel 60 $F_{254}$ aluminum backed plates (visualization using aq $KMnO_4$ stain).

NMR $^1H$ and $^{13}C$ NMR analysis was performed using a Bruker AM300 spectrometer. Chemical shifts are quoted in ppm relative to the solvent peak (CDCl3).

The following are non-limiting examples for producing cyclic amino alcohols of the instant invention.

EXAMPLE 1

Synthesis of keto oxime 2a

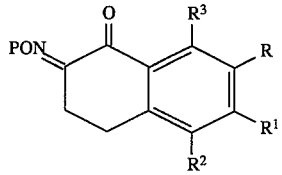

2a (P = H, R — $R^3$ = H)

Hydrogen chloride gas was bubbled slowly through a cold (−5° C.) stirred solution of 1-tetralone (10 g, 68 mmol) in isopropyl alcohol (200 mL) for 1 min. Isoamyl nitrite (10.1 mL, 75 mmol) was slowly added to the mixture, at a rate such that the solution temperature did not exceed 0° C. (approx. 10 min). Hydrogen chloride gas was periodically bubbled through the mixture until the reaction was complete. During this time the solution temperature was maintained below 0° C. (toward completion of the reaction the product began to crystalize). The mixture was filtered and the solid was washed with cold (0° C.) isopropyl alcohol (10 mL) to give 6 g of product. The filtrate and washings were combined and were then partitioned between EtOAc (100 mL) and $H_2O$ (100 mL). The layers were separated and the aqueous layer was extracted with EtOAc (50 mL). The combined organic extracts were washed with brine, dried ($MgSO_4$) and concentrated to give 5 g of product. The combined product was then re-crystallized from ethyl acetate-hexane (1:2) to give 9.5 g of 2a (79%) as a bright yellow solid. $^1H$ nmr (300 MHz, $CDCl_3$), 3.07 (2H, m), 3.19 (2H, m), 7.29 (1H, d, J=7.6 Hz), 7.37 (1H, m), 7.56 (1H, dd, m), 8.12 (1H, d, J=7.7 Hz). 11.02 (1H, br s). $^{13}C$ nmr (75 MHz) 23.3, 26.7, 127.3, 128.4, 128.7, 133.3, 134.3, 143.4, 152.8, 183.0.

Synthesis of keto-oxime ether 2b

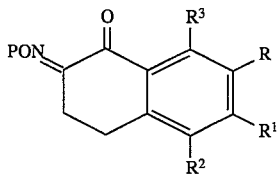

2b (P = TBS, R — $R^3$ = H)

To a cold (0° C.), stirred solution of the keto oxime 2a (24.8 g, 142 mmol) and tert-butyldimethylsilyl chloride (23.5 g, 156 mmol) in dry $CH_2Cl_2$ (200 mL) was added imidazole (24.1 g, 355 mmol). The mixture was allowed to warm to 25° C. and was stirred at this temperature for 30 min. Water (200 mL) was added, the layers were separated and the organic layer was washed with saturated aqueous $NaHCO_3$ (100 mL). The solution was concentrated to give an oil, which was purified by silica gel chromatography (95% hexane: 5% EtOAc) to give 31 g (76%) of keto oxime ether 2b, a yellow solid. $^1H$ nmr (300 MHz, $CDCl_3$), 0.26 (6H, s), 0.96 (9H, s), 2.99 (2H, m), 3.12 (2H, m), 7.24 (1H, d, J=7.6 Hz), 7.32 (1H, m), 7.47 (1H, m), 8.07 (1H, d, J=7.6 Hz). $^{13}C$ nmr (75 MHz) −5.1, 18.2, 24.0, 25.8, 26.0, 27.0, 127.2, 128.2, 128.5, 133.9, 143.1, 157.8, 183.2.

Synthesis of (1S,2R)-cis amino alcohol 1a

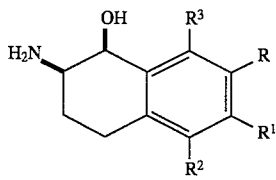

1a (R — $R^3$ = H)

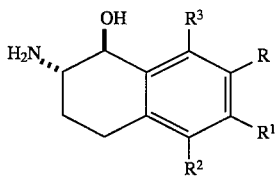

1b (R — $R^3$ = H)

To a cold (−20° C.), stirred solution of OAB-$BH_3$ complex (75.4 mg, 0.26 mmol, 10 mol %) and $BH_3.SMe_2$ (0.66 mL, 6.6 mmol, 2.5 equiv.) in toluene (7 mL, water content<20 μg/mL) was slowly added (over 4 h) a solution of the keto-oxime ether 2 (763 mg, 2.6 mmol) in toluene (7 mL). The mixture was stirred at −20° C. for 1 h and at 25° C. for 1 h and was then heated at 80° C. overnight. Methanol (30 mL) was added, the mixture was refluxed for 30 min and was then concentrated. The residue was redissolved in methanol (30 mL), refluxed for 30 min and concentrated to give a crude oil which was then purified by silica gel chromatography (85% $CH_2Cl_2$:13.5% MeOH: 1.5% $NH_4OH$) to give the amino alcohols 3 and 4 (387 mg, 90%) as a white solid. Analysis of the mixture by chiral HPLC (using a Crownpak CR(+) column, eluting with pH 2 $HClO_4$, detection at 220 nm) indicated a 6:1 ratio of 1a (91% ee):1b (75% ee). $^1H$ nmr analysis of the mixture confirmed this diastereomer ratio.

The absolute configurations of 1a and 1b were determined by conversion of the reduction mixture into the known R-amino tetralin 5:

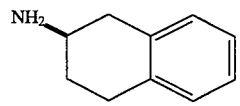

5

What is claimed is:

1. A process for the preparation of a compound represented by formula Ia or Ib:

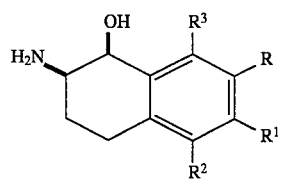

Ia

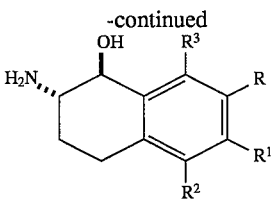

the individual diastereomers, the individual enantiomers or mixtures thereof, or acceptable salt thereof, wherein:

R, R$^1$, R$^2$ and R$^3$ are independently H, C1 to C10 alkyl, O-alkyl, alkylamino, thioalkyl, alkene, cycloalkyl or halogen;

comprising the steps of adding, over a course of about 3 to about 6 hours, a solution, containing a solvent and from about 0.05M to about 5.0M of a keto-oxime ether of the formula II:

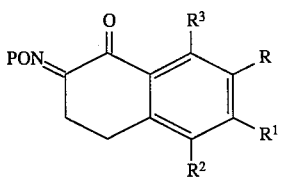

wherein P is H, TBS, TBDPS, acetate, benzoate, benzyl, paramethoxybenzyl (PMB), or alkyl; and R, R$^1$, R$^2$ and R$^3$ are independently H, C1 to C10 alkyl, O-alkyl, alkylamino, thioalkyl, alkene, cycloalkyl or halogen;

to a stirred and chilled solution of about 2 to about 30 mol % of an OAB-BH$_3$ complex and excess BH$_3$.SMe$_2$ in a solvent, stirring the mixture, heating the mixture until a substantial amount of Ia or Ib is produced and isolating the compound so produced.

2. The process of claim 1 wherein P is TBS, or TBDPS, the amount of OAB-BH3 is from about 2 to about 30 mol %, the amount of excess BH3.SMe2 is from about 1.0 to 4.0 equivalents, the solvent belongs to a group consisting of toluene, methylene chloride, THF, or hexane, and the mixture is stirred at from about −30° C. to about 0° C. for about 0.5 to about 2 hours and at room temperature for about 0.5 to about 2 hours, and heated at a temperature of about 50° C. to about 90° C.

3. The process of claim 2 wherein the BH$_3$.SMe$_2$ is added over the course of 2 to 6 hours to a mixture of the ketone and OAB-BH$_3$ catalyst.

4. The process of claim 2 wherein the BH$_3$.SMe$_2$ and keto-oxime ether is simultaneously added, over the course of 2 to 6 hours, to the OAB-BH$_3$ catalyst.

5. The process of claim 2 wherein the solvent is toluene, P is TBS or TBDPS, and the mixture is stirred at from about −22° C. to about −5° C. for about 0 to about 1 hour and at room temperature for 0 to about 1 hour, and heated at about 75° C. to 85° C.

6. The process of claim 1 where R and R1, independently are O-alkyl, and wherein after the compound has been isolated it is hydrogenated with from about 2 to about 7% Pt/C, MeOH-NH$_4$OH.

7. A process for the preparation of a compound represented by formula Ia or Ib:

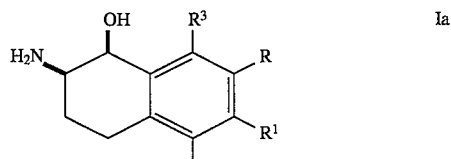

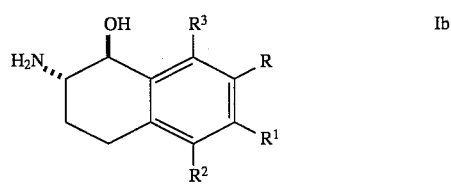

the individual diastereomers, the individual enantiomers or mixtures thereof, or acceptable salt thereof, wherein:

R, R$^1$, R$^2$ and R$^3$ are independently H, C1 to C10 alkyl, O-alkyl, alkylamino, thioalkyl, alkene, cycloalkyl or halogen;

comprising the steps of simultaneously adding an excess, from about 2 to about 4 equivalents, of BH$_3$.SMe$_2$ and from about 0.05M to about 0.5M of a keto-oxime ether of structural formula II:

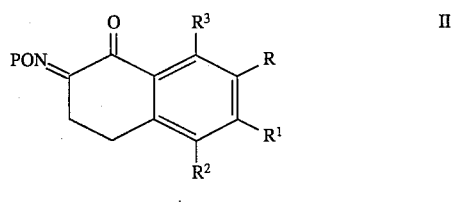

wherein:

P is H, TBS, TBDPS, acetate, benzoate, benzyl, paramethoxybenzyl (PMB), or alkyl; and R, R$^1$, R$^2$ and R$^3$ are independently H, C1 to C10 alkyl, O-alkyl, alkylamino, thioalkyl, alkene, cycloalkyl or halogen;

over the course of 2 to 6 hours, to from about 2 to about 30 mol % of a stirred and chilled solution of OAB-BH$_3$ catalyst, stirring the mixture, heating the mixture until a substantial amount of formula Ia or Ib is produced and isolating the compound so produced.

* * * * *